United States Patent
Mamraev

(10) Patent No.: US 8,827,702 B2
(45) Date of Patent: Sep. 9, 2014

(54) DRIVER AND METHOD

(75) Inventor: Meir Mamraev, Rishon Lezion (IL)

(73) Assignee: Cortex Dental Implant Industries, Ltd., Industrial Zone Shlomi (IL)

( * ) Notice: Subject to any disclaimer, the term of this patent is extended or adjusted under 35 U.S.C. 154(b) by 0 days.

(21) Appl. No.: 13/137,765

(22) Filed: Sep. 12, 2011

(65) Prior Publication Data

US 2013/0065197 A1 Mar. 14, 2013

(51) Int. Cl.
*A61C 3/00* (2006.01)
*A61C 8/00* (2006.01)

(52) U.S. Cl.
CPC ............. *A61C 8/0087* (2013.01); *A61C 8/0089* (2013.01)
USPC ............ 433/147; 433/163; 433/173; 206/368

(58) Field of Classification Search
USPC .............. 433/172–176, 201.1, 141, 146–147, 433/163–164; 206/368, 369, 438, 63.5
See application file for complete search history.

(56) References Cited

U.S. PATENT DOCUMENTS

| | | | | |
|---|---|---|---|---|
| 6,068,478 A | * | 5/2000 | Grande et al. | 433/172 |
| 6,068,480 A | * | 5/2000 | Misch et al. | 433/173 |
| 6,261,097 B1 | | 7/2001 | Schmutz et al. | |
| 6,827,575 B1 | * | 12/2004 | Jorneus | 433/174 |
| 2002/0150862 A1 | * | 10/2002 | Day | 433/173 |
| 2003/0211445 A1 | * | 11/2003 | Klardie et al. | 433/173 |
| 2004/0096804 A1 | * | 5/2004 | Vogt et al. | 433/173 |
| 2008/0241792 A1 | * | 10/2008 | Rossler et al. | 433/174 |
| 2011/0014586 A1 | * | 1/2011 | Jorneus et al. | 433/173 |

FOREIGN PATENT DOCUMENTS

WO WO 02/30315 4/2002

* cited by examiner

*Primary Examiner* — Edward Moran
(74) *Attorney, Agent, or Firm* — Law Offices of Steven W. Weinrieb

(57) ABSTRACT

A driver assembly for driving a dental implant into an implantation site comprises a driver assembly and an abutment assembly. The lower portion of the driver assembly accommodates the upper portion of the abutment assembly in a rotation-preventing manner so as to prevent relative rotation between the driver assembly and the abutment assembly. In addition, the driver assembly includes a weakened section which permits the upper portion thereof to be separated from the lower portion and discarded while the lower portion remains mounted upon the abutment assembly.

16 Claims, 12 Drawing Sheets

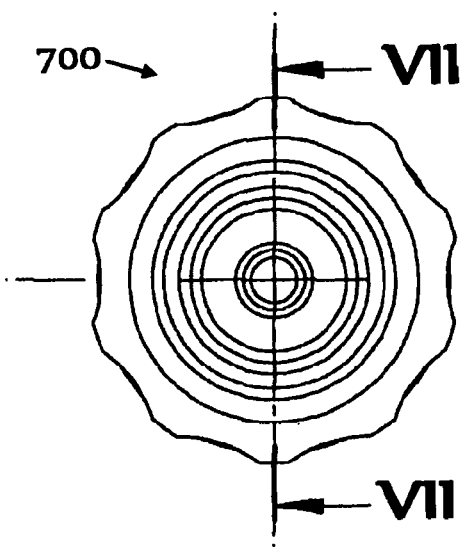
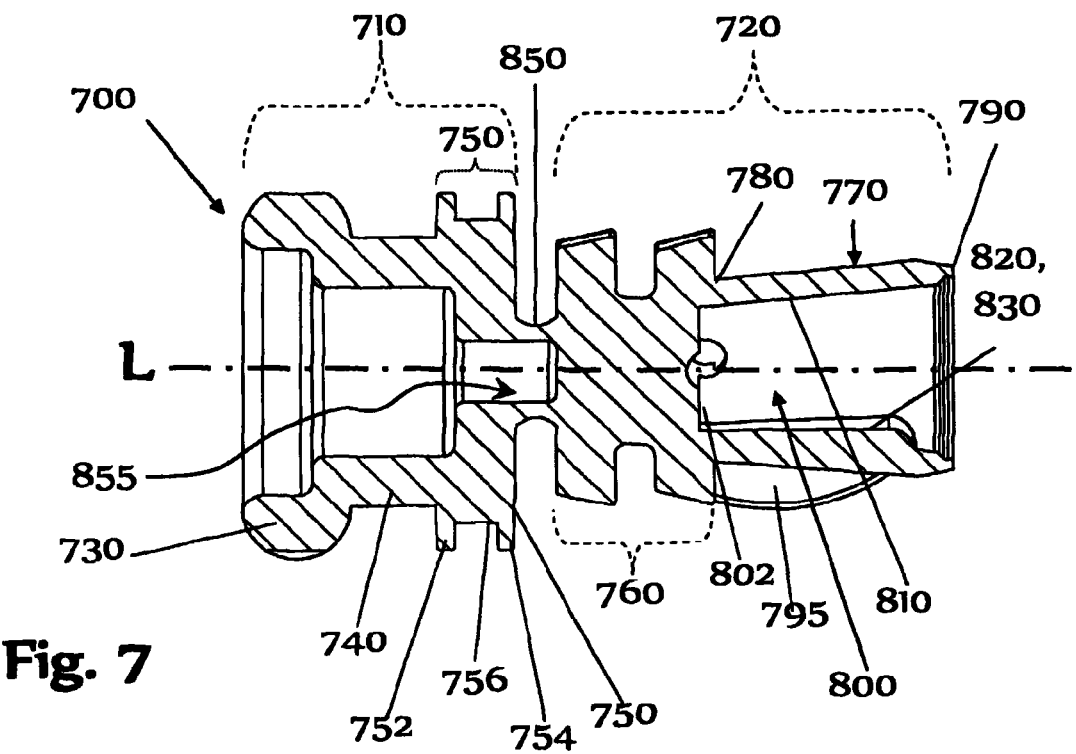
Fig. 6
Fig. 7

DRIVER AND METHOD

FIELD OF THE INVENTION

The present invention is broadly related to a package for preserving a medical device or the like, and in particular to a package with a canister for preserving a dental implant, the canister being provided with a driver assembly designed to carry the dental implant to an implantation site, to minimize the danger of contamination of the dental implant, the driver assembly being contained within the canister.

It is expected that the use of the new method and driver may offer ad-vantages of eliminating a need to obtain a separate driver and/or transfer, eliminating the usage of a metal driver and/or transfer, and/or eliminating metal-to-metal contact which helps to alleviate galvanic currents, ion exchange, and/or other phenomena, which may possibly harm osseointegration.

BACKGROUND OF THE INVENTION

Examples brought to light henceforth of related art and any/or all limitations related therewith are intended to be illustrative and not exclusive. Other limitations of the related art will become apparent to those of skill in the art upon a reading of the specification and a study of the figures. An illustrative ex-ample of a procedure that uses these canisters may be a dental prosthesis using embedded anchoring elements which may be accommodated within canisters the likes of which may be disclosed hereinbelow. However, such exemplary and illustrative purpose, and the related description and drawings herein, should be interpreted by way of illustrative purpose without limiting the scope and sprit of the present invention. Other types of procedures may well be considered as applicable for the utilization of the presently disclosed canister, driver and/or method.

Dental implants may be typically packaged as an assembly including all the tools necessary for the insertion of the implant into an osteotomy formed in the jaw. A typical threaded implant assembly may include a threaded implant body, an implant carrier, an insertion post, a coupling screw and a healing cap. Conventionally, these components are sterilized, pre-assembled and packaged in a sterile vial. The implant carrier, insertion post, and coupling screw are tools which may be used during the insertion of the implant body. Typically, the implant carrier, insertion post, coupling screw and vial may be discarded after the implant body has been inserted into the osteotomy. The healing cap seals and protects the central socket of the implant body during the initial healing period, and then it may, too, be discarded.

During the insertion of a conventional threaded implant, the insertion post may be mechanically coupled to the top of the implant body by a coupling screw which traverses a central through-cavity in the insertion post and may be threaded into the central threaded socket in the implant body. Typically, the bottom end of the insertion post may be formed with a hexagonal cavity that non-rotationally mates with a corresponding hexagonal protrusion which may be formed on the top of the implant body thereby preventing any relative rotation between the insertion post and implant body while coupled.

An implant carrier may be releasably coupled to the top of the insertion post and provides the dental practitioner with a means to grip and manipulate the assembly during the initial implantation procedure. Typically, the implant carrier may be formed with a generally hexagonal internal passage at its bottom end which mates with a generally hexagonal outer surface near the top of the insertion post. The dental practitioner may use the implant carrier to manipulate the implant body into the proper location within the jawbone. Torque is then applied to the implant carrier which is transferred, by means of the insertion post, to the threaded implant body.

In use, an osteotomy may be drilled in the jawbone. The implant carrier may then be used to transport the threaded implant assembly to the surgical site. The implant carrier may be gripped by the practitioner and may be used to manipulate the implant body into the correct position and then to partially screw the threaded implant body into the osteotomy.

Once the implant body has been initially placed in the osteotomy and tightened manually, the implant carrier may be decoupled from the insertion post and may be removed from the surgical site. If necessary, a suitable wrench or dental handpiece is then used to engage the insertion post and drive the implant to its final depth within the osteotomy. The coupling screw is then removed and the insertion post is decoupled from the implant body leaving only the implant body in the patient's mouth.

At a stage subsequent to the implantation and healing, an impression may be taken of the patient's mouth in order to fabricate a prosthesis or dental restoration. An abutment supporting the final restoration is then attached to the implant body. Lastly, the restoration is cemented or screwed to the abutment and/or implant body to complete the placement of the prosthodontic restoration in the patient's mouth.

The procedure described above for installing a threaded dental implant is commonly used by dental practitioners. However, this procedure suffers from several significant shortcomings. For example, the dental practitioner may choose to attach a wrench or dental handpiece to the threaded implant assembly before transporting the assembly to the surgical site. The dental practitioner may choose to modify the procedure in this manner because it can be difficult to attach the wrench or dental handpiece to the implant assembly in-side the patient's mouth. This modification requires the dental practitioner to remove the implant carrier from the implant assembly by gripping the implant assembly with one hand and pulling the implant carrier away from the implant assembly with the other hand. Typically, the wrench or dental handpiece may then be attached to the implant assembly by gripping the implant assembly with one hand while pushing the wrench or handpiece towards the dental assembly with the other hand. This procedure may be undesirable for several reasons. For example, touching the implant assembly can damage and/or contaminate the assembly. This procedure may also require an additional step of removing the implant carrier from the implant assembly.

A package with an external capsule for preserving a dental implant is known, as an example only, from U.S. Pat. No. 6,261,097 which discloses, inter alia, as shown in the associated drawings as FIG. 1 Prior Art, "an implant 1 and a holding element 100 with an extension element 121 releasably associated with the implant 1. In the assembled state, an ampule 200, with the implant 1 held therein by the holding element 100, is inserted into a capsule 300. The capsule 300 comprises a hollow cylinder 310, the base 311 of which is closed, and a screw-on closure cap 320. On the inside of the cylinder 310, parallel to and at a distance from the base 311, there is a support shoulder 313, which is intended to act as an axial stop for the first planar base side on a fixing part 210 of the inserted ampule 200. At most in the region of the clearance between the second planar base side on the stand part 220 and the closure cap 320, the ampule 200 can move on the axis M and otherwise lies in a stable position in the capsule 300 in the event of vibrations.

"The implant 1 is held by a holding element 100 with a screw 101 and a sleeve part 102. An externally threaded part 131 of the screw 101, which projects through the sleeve part 102, engages an internally threaded bore 14 on the implant 1, while a mating shoulder 161 of a shoulder part 160 of the sleeve part 102 rests upon an implant shoulder. A fixing part 110 of the holding element 100 is latched into the fixing part 210 of an ampule 200, that is, the cylindrical section 116 of the holding element 100 is clamped in a laterally open indent 212 in the ampule 200 and is surrounded laterally by the two jaws 215, 216. Annular shoulders of the holding element 100 bear against the fixing part 210 on both sides. In this way, the implant 1 is held in line with the center axis M inside the ampule 200 without coming into contact with the ampoule 200".

Another capsule or package for a dental implant is known from PCT patent publication WO 0230315. The known package according to this patent publication WO 0230315 comprises a protective housing and a holder arranged to support the dental implant spaced from the lateral walls of the protective housing. The holder is arranged for sliding motion into and out of the protective housing, such that, when the holder is extracted from the housing, it allows access to the dental implant.

Thus, there exists a need in the industry for an improved delivery system for dental implants. It would be desirable to have a canister and/or driver that may be used to transport, deploy and/or controllably release an implant, in particular, and/or any other relevant medical component, in more general terms, on designated sites. An associated method therefore, which may facilitate the above, is also needed. It is expected that the use of the new method and/or driver may also offer advantages of eliminating a need to obtain a separate driver or transfer, of eliminating the usage of a metal driver or transfer, and of eliminating any metal-to-metal contact which helps to alleviate galvanic currents, ion exchange, and/or other phenomena which might harm osseointegration (see http://en.wikipedia.org/wiki/Osseointegration), incorporated herein by reference. This may be attained with the subject matter in accordance with the claims.

SUMMARY OF THE INVENTION

In the following disclosure, aspects thereof are described and illustrated in conjunction with systems and methods which are meant to be exemplary and illustrative, not limiting in scope. In various embodiments, one or more of the above-described issues and/or desirable effects have been addressed, while other aspects are directed to effect other advantages or improvements.

In view of the foregoing it is an object of the present disclosure to discuss providing for a package for preserving a medical device, in particular an implant, which may provide for the safe and easy handling of the medical device or the implant prior to deployment on the designated site.

According to one aspect of the present disclosure, there is provided a driver assembly comprising a driver and an abutment; the driver comprises a bottom section which, in turn, comprises a skirt; the skirt comprises a cave formed therein, with the cave comprising a step having a step-face; the abutment comprises a top member and a mid member, with the top member comprising a flat face; the top member is designed to be accommodated in the cave, with the flat face of the abutment abutting the step-face of the driver, to prevent relative rotation between the bottom section of the driver and the top member of the abutment.

Optionally, the driver may be manufactured from a resilient and/or non-metallic material. Furthermore, the driver may be monolithic, that is, manufactured as a single one piece.

Potentially, the skirt the of driver may comprise a welt having an inner welt wall extending away from a terminus at a bottommost longitudinal extent of the driver to meet, and merge with, an inner cave-wall.

The welt inner wall may comprise a generally diverging frusto-conical first sector adjacent to and merging with the cave-wall, and a generally converging frusto-conical end sector adjacent to, and merging with, the terminus. Furthermore, the first sector may diverge from a cave mouth dimension $D_C$ to a first dimension $D_F$. Moreover, the end sector may converge from the first dimension $D_F$ to an end dimension $D_E$.

Alternatively, the top member may extend away from a top tip to merge with a mid member by means of an expansion, with the expansion being gene-rally shaped as a frustum starting with a small dimension transverse to the longitudinal axis L identical to a base dimension $D_B$ of the top member and expanding to a hump dimension $D_H$ at a hump. Further, the hump may connect the expansion to the mid member, while the mid member may extend from the hump away from the top member towards a bottom member as it converges from the hump dimension $D_H$ to a grab dimension $D_G$.

Continuing further, the cave of the driver may be designed to accommodate the top member and the hump of the abutment, with the welt of the driver resiliently grabbing a grab zone disposed upon the mid member. Furthermore, the grab zone may extend away from adjacent the hump along the mid member, and/or the grab zone may be defined as a region where the end sector grabs a portion of the mid member adjacent the hump.

Optionally, the grab dimension $D_G$ is smaller than the hump dimension $D_H$, and is larger than the end dimension $D_E$ of the end sector.

The driver may also comprise a top section interconnected to the bottom section by a weakened stem.

According to another aspect of the present disclosure, there is disclosed a method for transporting and driving an implant into an implantation site, the method comprising the steps of: providing an abutment connected to the implant, the abutment comprising a top member, the top member comprising a flat face; providing a driver having a cave formed therein, the cave comprising a step having a step-face; inserting the abutment into the cave with the flat face urged onto the step-face, to prevent relative rotation therebetween; and applying torque to the driver, thereby causing the abutment to turn.

The method may further comprise the step of providing a weakened stem interconnecting the bottom section and a top section, wherein, upon exceeding a predetermined torque, the stem snaps off.

In addition to the exemplary aspects described above, further aspects and embodiments will become apparent by reference to the figures and by study of the following detailed descriptions.

BRIEF DESCRIPTION OF DRAWINGS

An exemplary embodiment will be illustrated in the referenced figures and drawings. It is intended that the figures disclosed herein are to be considered illustrative rather than restrictive. It is emphasized that, according to common practice, the various features of the drawings are not to scale, but rather dimensions of various features are arbitrarily expanded or reduced for clarity.

Reference will now be made to the accompanying drawings, in which:

FIG. 6 schematically illustrates a plan view of the driver of the package shown in FIGS. 2 and 3;

FIG. 7 schematically illustrates a longitudinal cross-sectional view of the driver shown in FIG. 6 as taken along lines VII-VII;

DETAILED DESCRIPTION OF THE PREFERRED EMBODIMENT

Packaging

Figure 1:
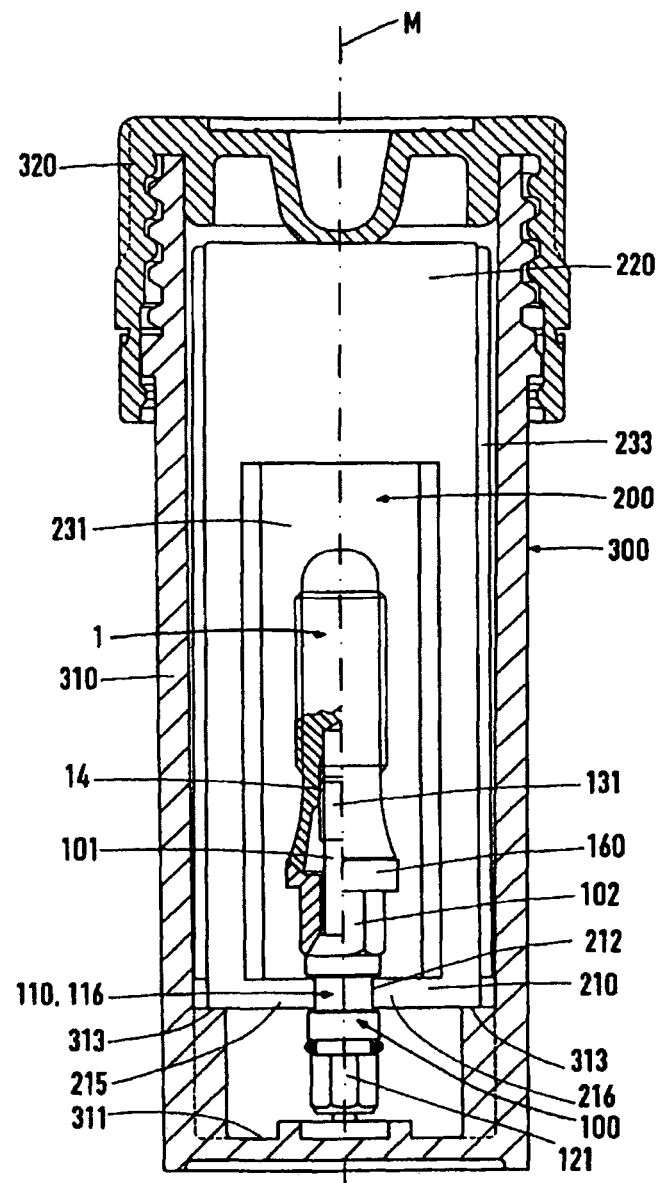
FIG. 1 Prior Art illustratively depicts FIG. 10 of U.S. Pat. No. 6,261,097.
Figure 2:
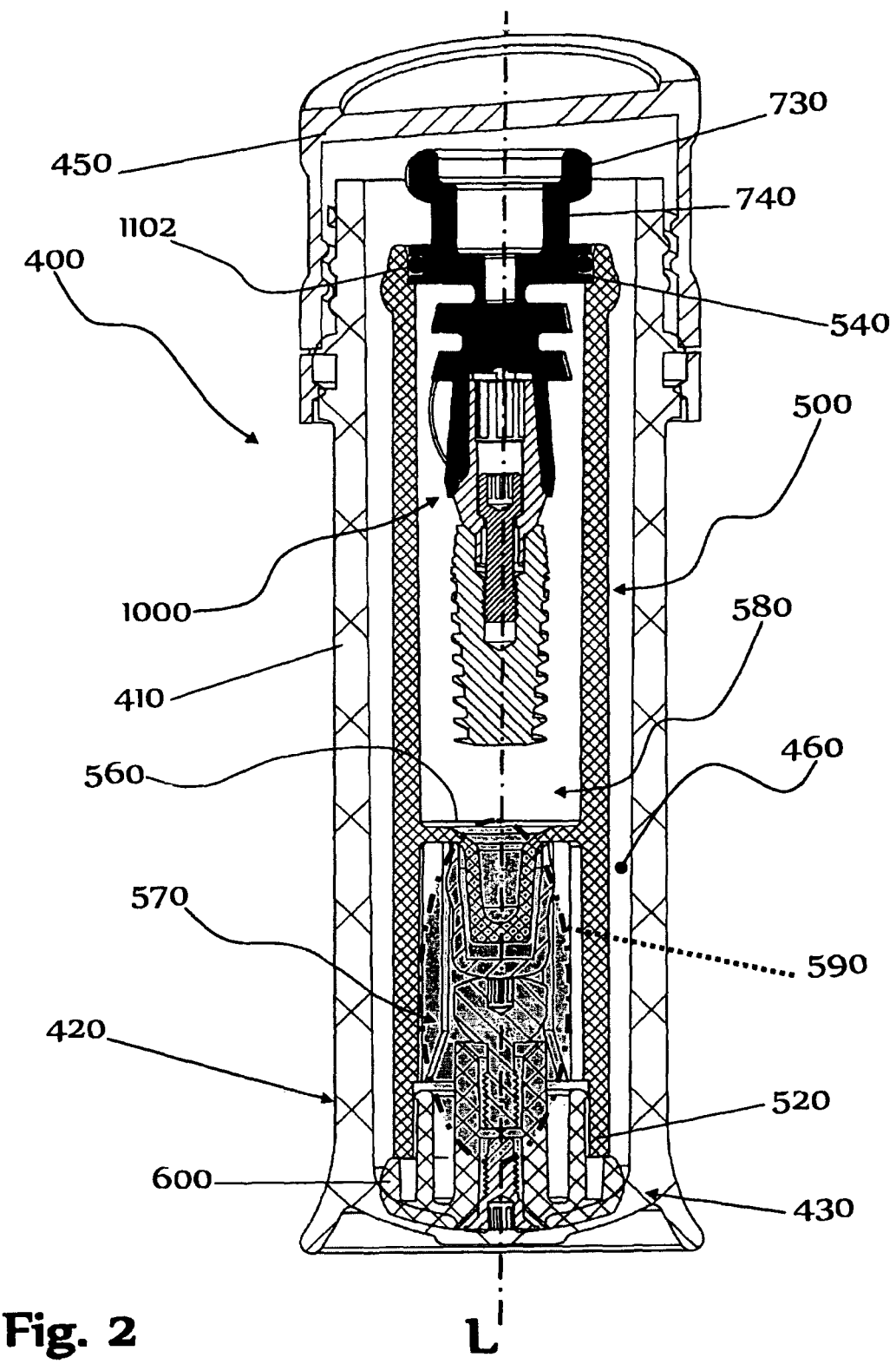
FIG. 2 schematically illustrates a longitudinal cross-sectional view taken in a plane comprising the longitudinal axis L through the packaging, the canister, the driver, the implant assembly and associated accessories in accordance with an embodiment of the present invention.
Figure 3:
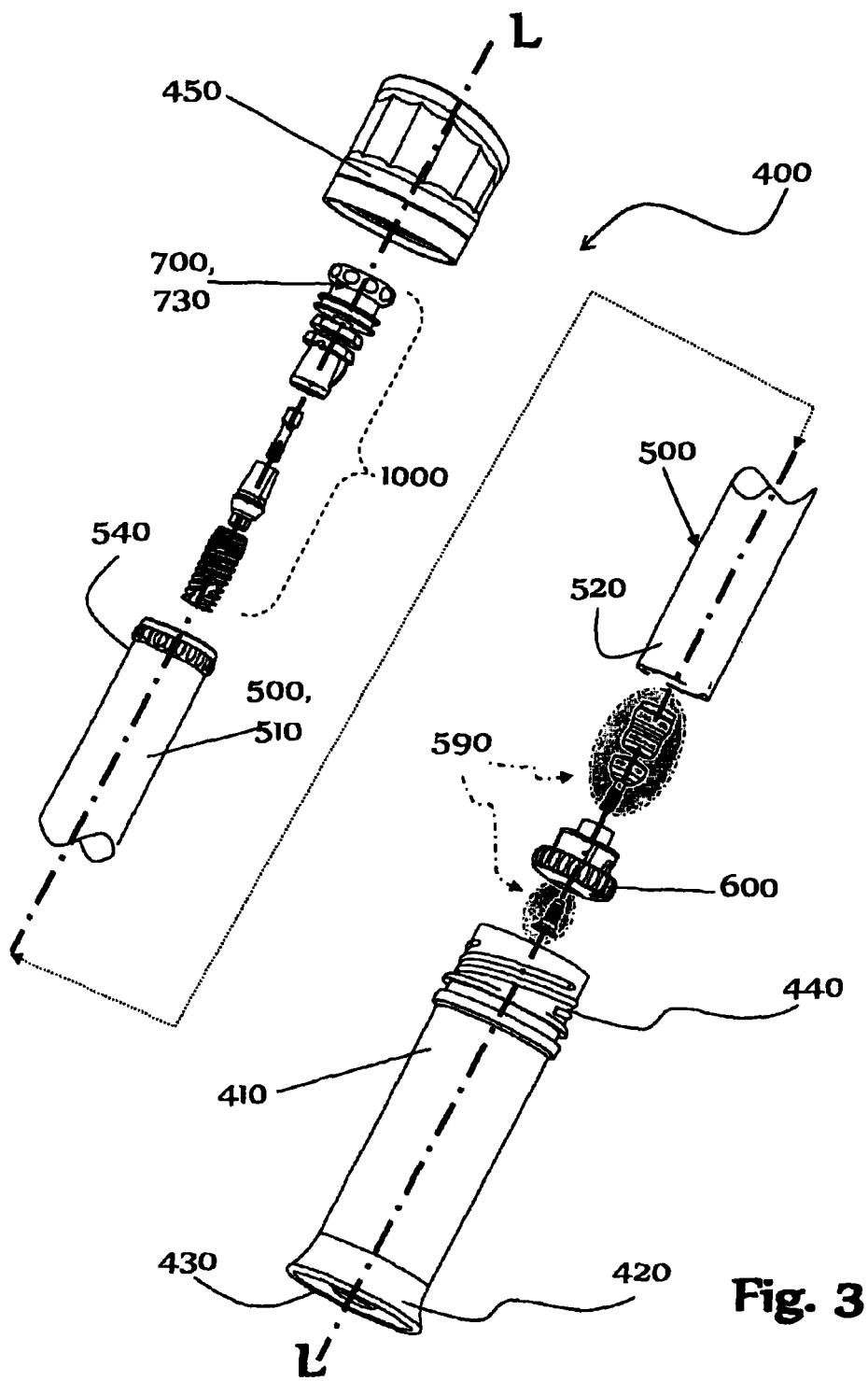
FIG. 3 schematically illustrates a perspective exploded assembly view of some of the components comprising the package shown in FIG. 2.

Attention is presently drawn to FIGS. 2 and 3. A packaging 400 extends generally longitudinally along a longitudinal axis L and comprises an elongated fuselage 410 terminated at a first end 420 thereof by a cover 430. A second end 440 generally opposing the first end 420 may have a lid 450. The cover 430 may be either integral with, or removable from, the fuselage 410, while the lid 450 may generally be removable from the fuselage 410, in any number of known and/or discovered applicable ways and/or manners.

Figure 4:
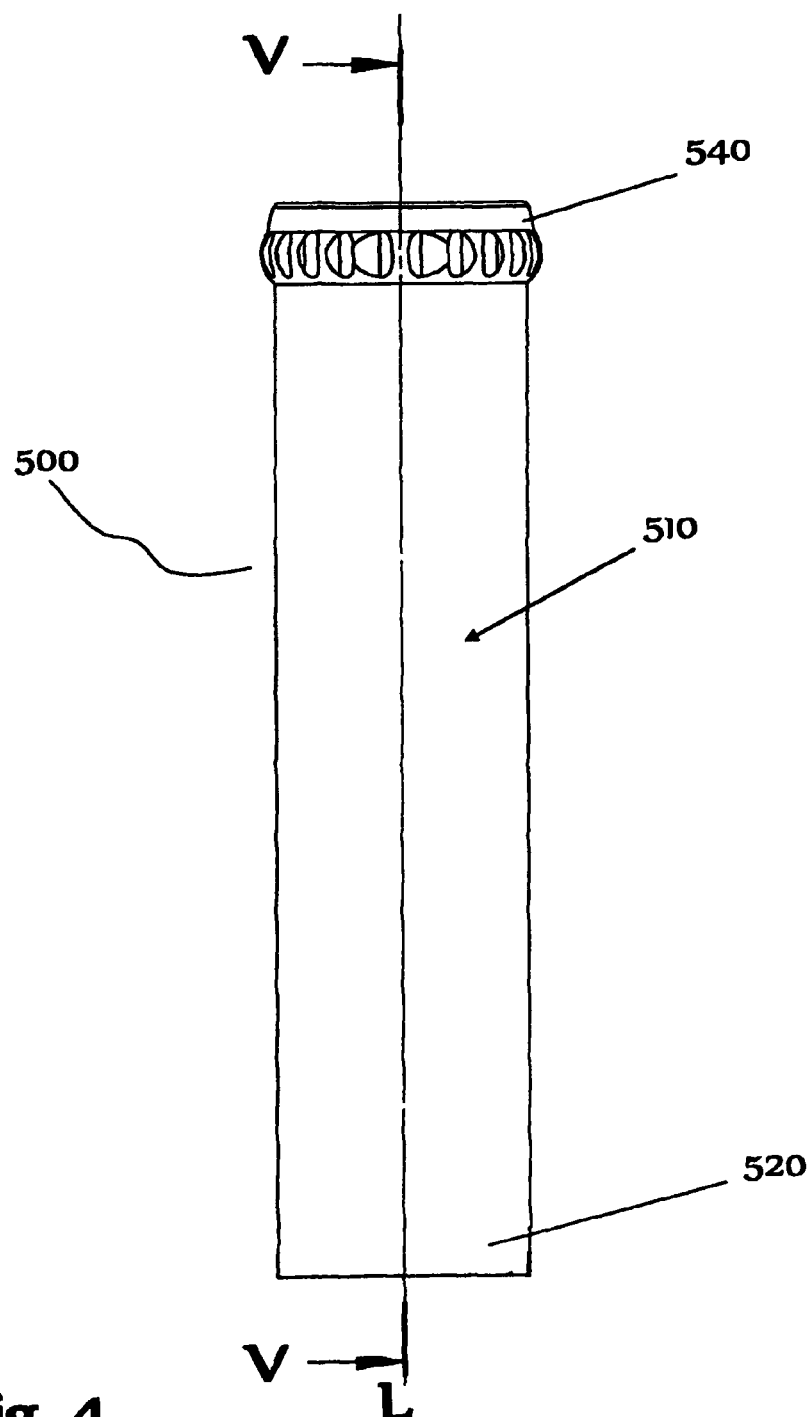
FIG. 4 schematically illustrates an elevation view of the canister shown in FIG. 2.

Drawing attention additionally to FIG. 4, the packaging 400 defines an inner space 460 removably accommodating a canister 500. The canister 500 comprises a generally cylindrical, hollow hull 510, extends generally longitudinally between a first opening 520 and a second opening 540. As the canister 500 is accommodated in the packaging 400, the first opening 520 may rest adjacent the first end 420 while the second opening 540 may rest adjacent the second end 440 and the lid 450 of the packaging 400.

Figure 5:
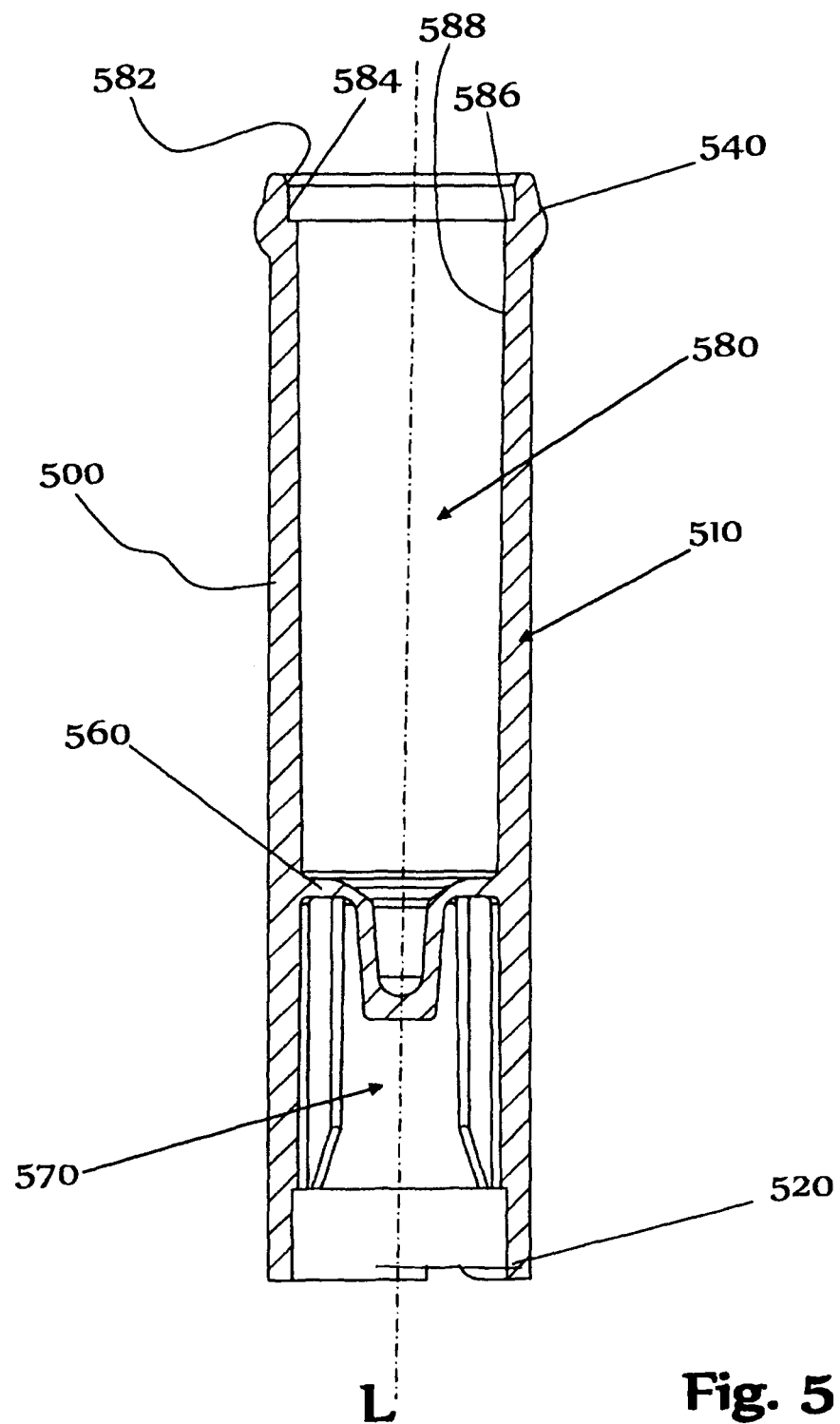
FIG. 5 schematically illustrates a longitudinal cross-sectional view taken in the plane comprising the longitudinal axis L along the lines V-V through the canister.

As may best be seen in FIG. 5, a look at a longitudinal cross-sectional view of the hull 510 of the canister 500 reveals that the hull 510 comprises a bulkhead 560 extending generally transversely to the longitudinal axis L dividing the hull 510 into two, not necessarily equal, chambers, a first chamber 570 extending away from the bulkhead 560 and toward the first opening 520, and a second chamber 580 extending away from the bulkhead 560 in a direction opposite to the first chamber 570 and toward the second opening 540.

Adjacent to the second opening 540 of the second chamber 580, there is disposed a generally frusto-conical guide 582 which opens into the second opening 540. The guide 582 converges as it extends away from the second opening 540 so as to merge with a generally longitudinally extending opening wall 584 which terminates at a generally radially inwardly extending step 586. The step 586 extends to, and terminates at, a generally cylindrical, longitudinally extending, chamber wall 588.

Returning now to FIGS. 2 and 3, the first chamber 570 may accommodate several items, commonly referred to as accessories 590. Such accessories may include, as a general example only, a cover screw, a healing screw, and/or other items which may be relevant to an implantation procedure. The first chamber 570 may be sealed by a removable cap 600 removably mounted over the first opening 520, while the second chamber 580 may be sealed by a re-movable driver 700 removably mounted within the second opening 540, as will be further elaborated hereinafter.

Driver

Figure 7A:
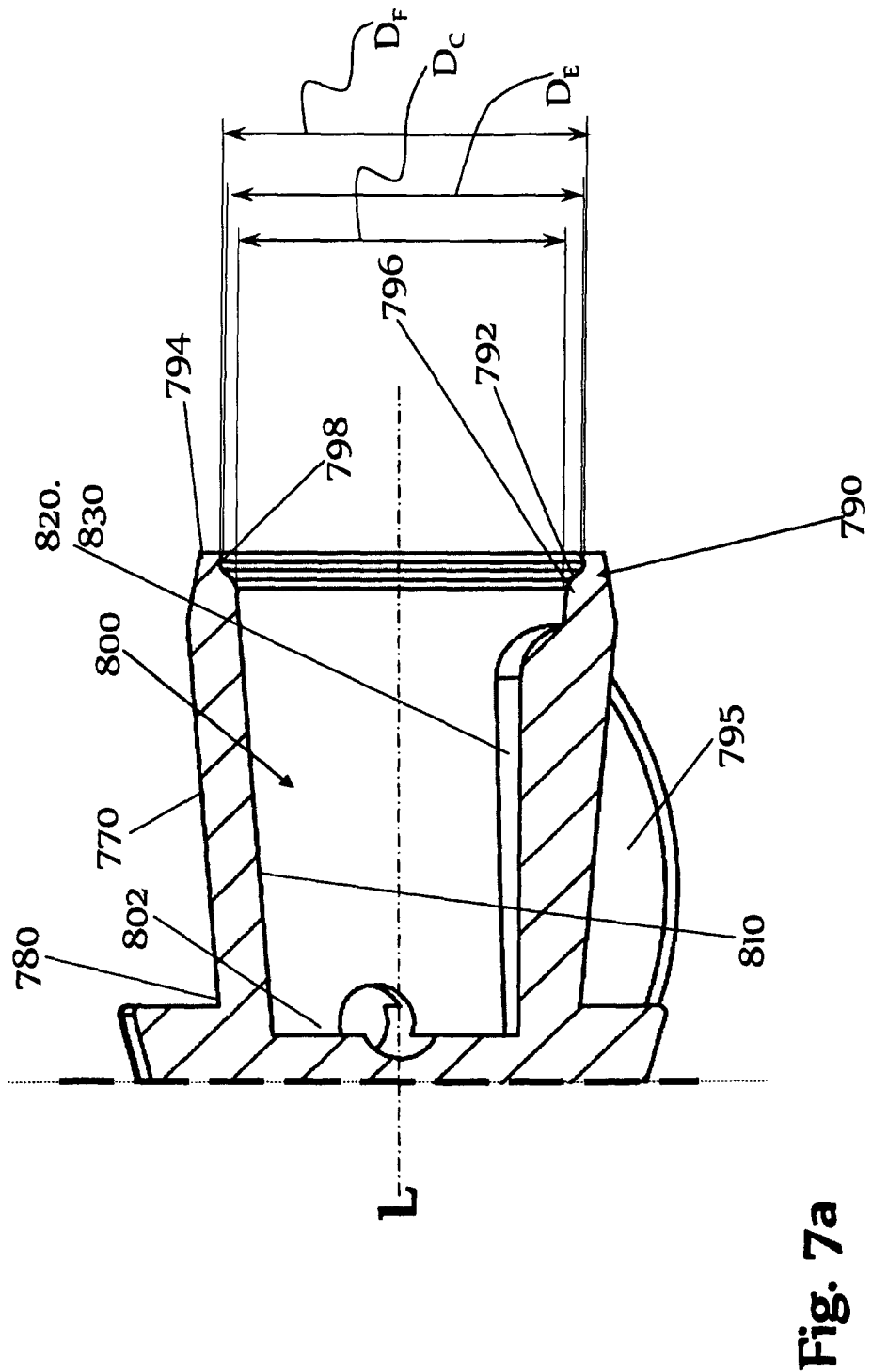
FIG. 7a schematically illustrates a detail view of the skirt of the driver shown in FIGS. 2 and 3.
Figure 8:
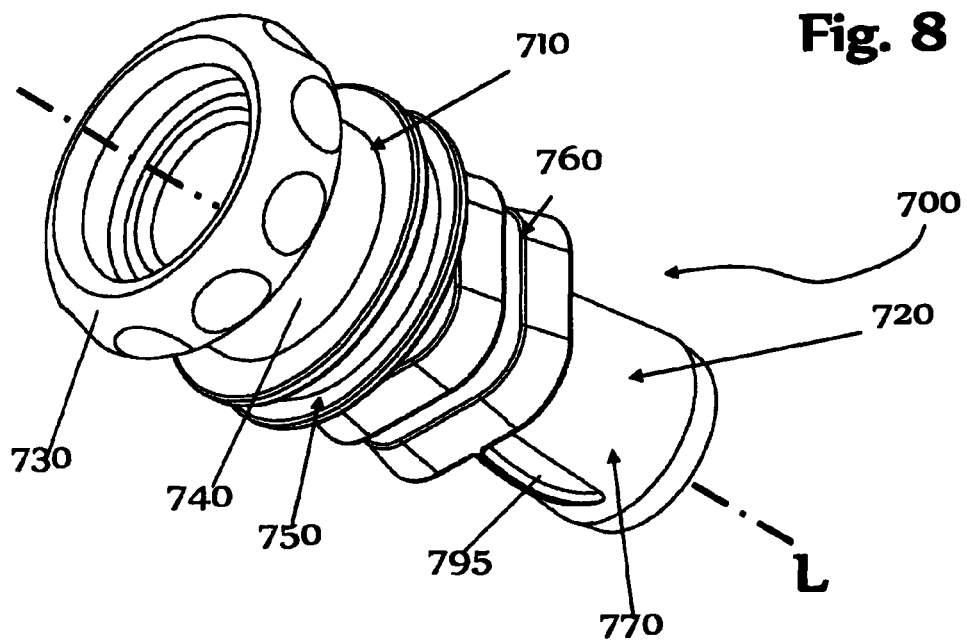
FIG. 8 schematically illustrates a top perspective view of the driver shown in FIG. 6.
Figure 9:
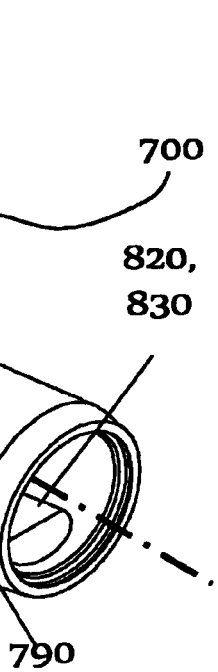
FIG. 9 schematically illustrates a bottom perspective view of the driver shown in FIG. 6.
Figure 10:
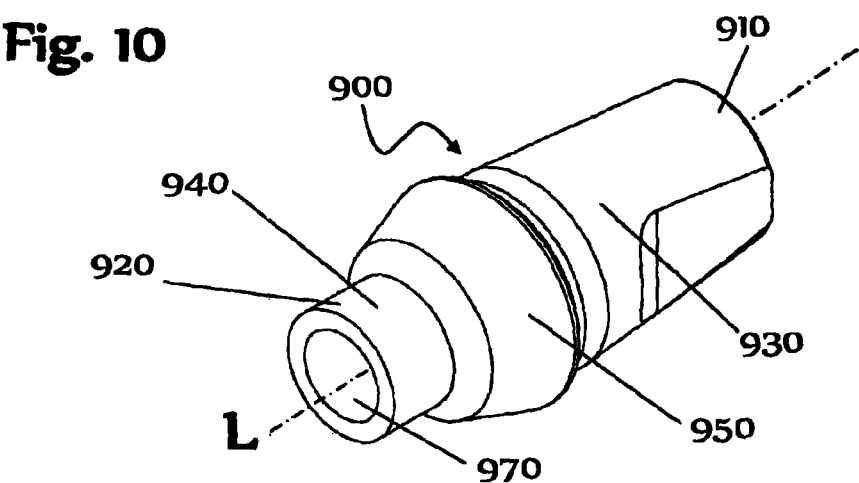
FIG. 10 schematically illustrates a bottom perspective view of an abutment forming a component of the package shown in FIG. 2.

The driver 700 may best be seen in FIGS. 6 to 9, with attention initially being made to FIGS. 8 and 9. The driver 700 may be manufactured from any somewhat resilient material, preferably a non-metallic, bio-compatible material, and may comprise a top section 710 and a bottom section 720 extending along the longitudinal axis L. The top section 710 terminates at a head 730 and extends away therefrom to a neck 740 linking the head 730 to a shoulder 750. The shoulder 750 comprises a top bank 752 and a bottom bank 754 separated longitudinally by a groove 756 designed to accommodate a seal 1102, as may best be seen in FIG. 2, such as, for example an O-ring seal.

The bottom section 720 extends longitudinally in a direction away from the bottom bank 754 and comprises a grip 760. A skirt 770, generally frusto-conical in its external shape, extends away from a waist 780 adjacent the grip 760 and connecting therewith, and diverges towards a welt 790. A generally longitudinal rib 795 merges with the grip 760 and extends away therefrom to terminate at the skirt 770. As may be best seen in FIG. 9, the skirt 770 comprises a generally hollow cave 800 having a generally frusto-conical inner cavewall 810 and opening in a direction away from the welt 790 so as to terminate at a generally transverse partition 802.

Attention is presently additionally directed to FIG. 6, showing a plan view of the driver 700, and to FIG. 7 which illustrates a longitudinal cross-section taken along the longitudinal axis L. Disposed between the top section 710 and the bottom section 720 and interconnecting the same therebetween, there is a stem 850 which may be integrally formed with both the top section 710 and the bottom section 720. The stem 850 may be weakened, for example by means of an inner bore 855 fashioned generally longitudinally along the top section 710 generally concentrically therethrough. However, other methods of weakening may be employed, including, but not limited to, slotting, punching transverse holes, and such. As may additionally be seen in FIG. 9, the cave 800 comprises a step 820 extending generally radially away from the cavewall 810, the step 820 having a generally planar step-face 830 expending generally parallel to the longitudinal axis L. The cave 800 is designed to accommodate and form-fit an abutment head, to be discussed below.

Details of the cave 800 and the welt 790 terminating the cave 800 may best be appreciated from FIG. 7a. The welt 790 comprises an inner welt wall 792 extending away from a terminus 794 at a bottommost longitudinal extent of the driver 700. The welt inner wall 792 extends to meet, and merge with, the cave-wall 810. The welt inner wall 792 comprises a generally diverging frusto-conical first sector 796 adjacent to and merging with, the cave-wall 810, and a generally converging frusto-conical end sector 798 adjacent to, and merging with, the terminus 794. The first sector 796 diverges from a cave mouth dimension $D_C$ to a first dimension $D_F$. The end sector 798 converges from the first dimension $D_F$ to an end dimension $D_E$.

Abutment

Attention is presently directed to FIGS. 10 to 12a. An abutment 900 which may be removably mounted as an extension of a dental implant (yet to be discussed) is shown in perspective in FIG. 10, in elevation in FIG. 11, and in plan in FIG. 12. The abutment 900 extends generally longitudinally from a top tip 910 to a bottom tip 920. The abutment 900 may be monolithic in construction, and may comprise a top member 930 adjacent the top tip 910 and a bottom member 940 extending away from the bottom tip 920 to meet with a mid member 950.

Figure 12:
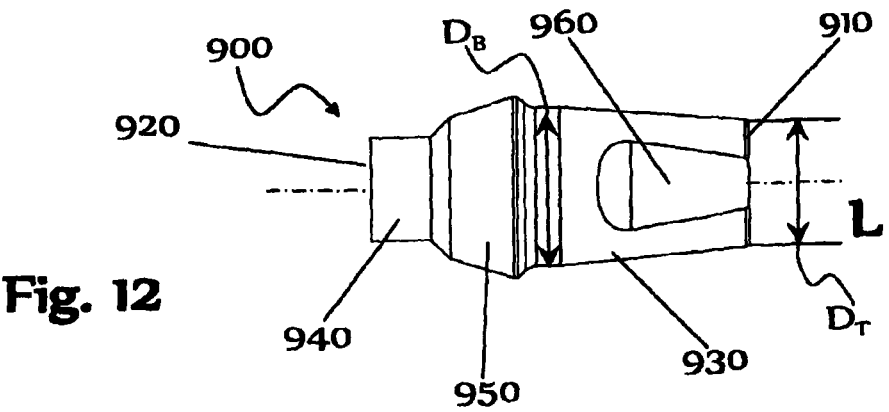
FIG. 12 schematically illustrates a plan view of the abutment shown in FIG. 10.

The top member 930 may be generally shaped as a frusto-conical member having a tip dimension $D_T$, as may best be seen in FIG. 12, transverse to the longitudinal axis L adjacent the top tip 910 which is smaller than a base dimension $D_B$ transverse to the longitudinal axis L adjacent the mid member 950. A generally planar flat face 960 may be formed onto the top member 930 parallel to the longitudinal axis L. The bottom member 940 may have any shape conforming to and/or appropriate to an implant, as will be discussed hereinafter. The abutment 900 may be formed with a through-bore 970, as will be elaborated further hereinbelow.

Figure 12A:
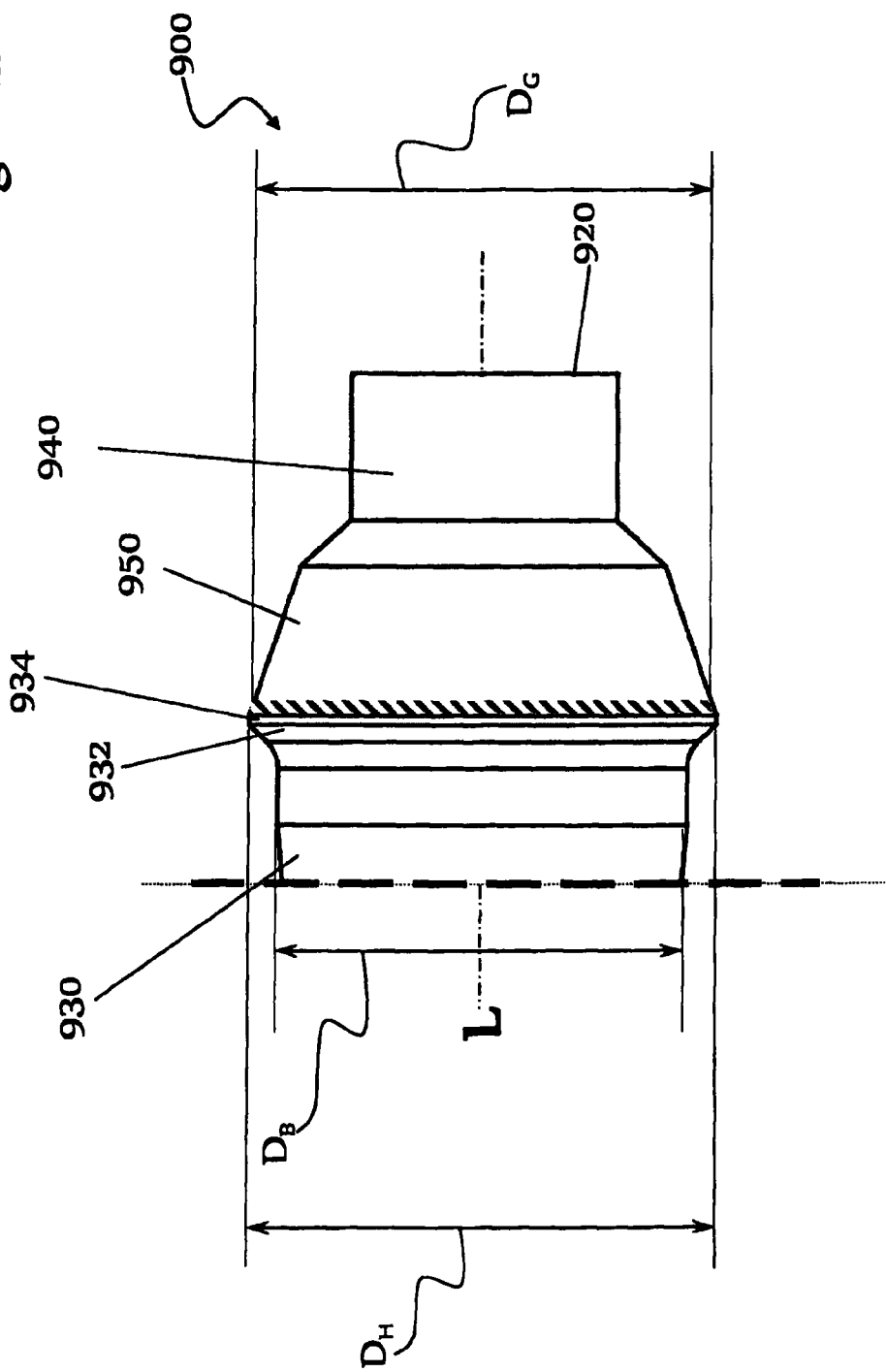
FIG. 12a schematically illustrates the details of the head of the abutment shown in FIG. 12.

As may be best seen in FIG. 12a, the top member 930 merges with the mid member 950 at an expansion 932 which may be generally shaped as a frustum starting with a small dimension transverse to the longitudinal axis L identical to the base dimension $D_B$ of the top member 930 and expanding to a hump dimension $D_H$ at a hump 934 connecting the expansion 932 to the mid member 950. The mid member 950 extends from an axial position adjacent to the hump 934 towards the bottom member 940, converging from the hump dimension $D_H$ as it extends away from the hump 934.

Driver Assembly

Figure 13:
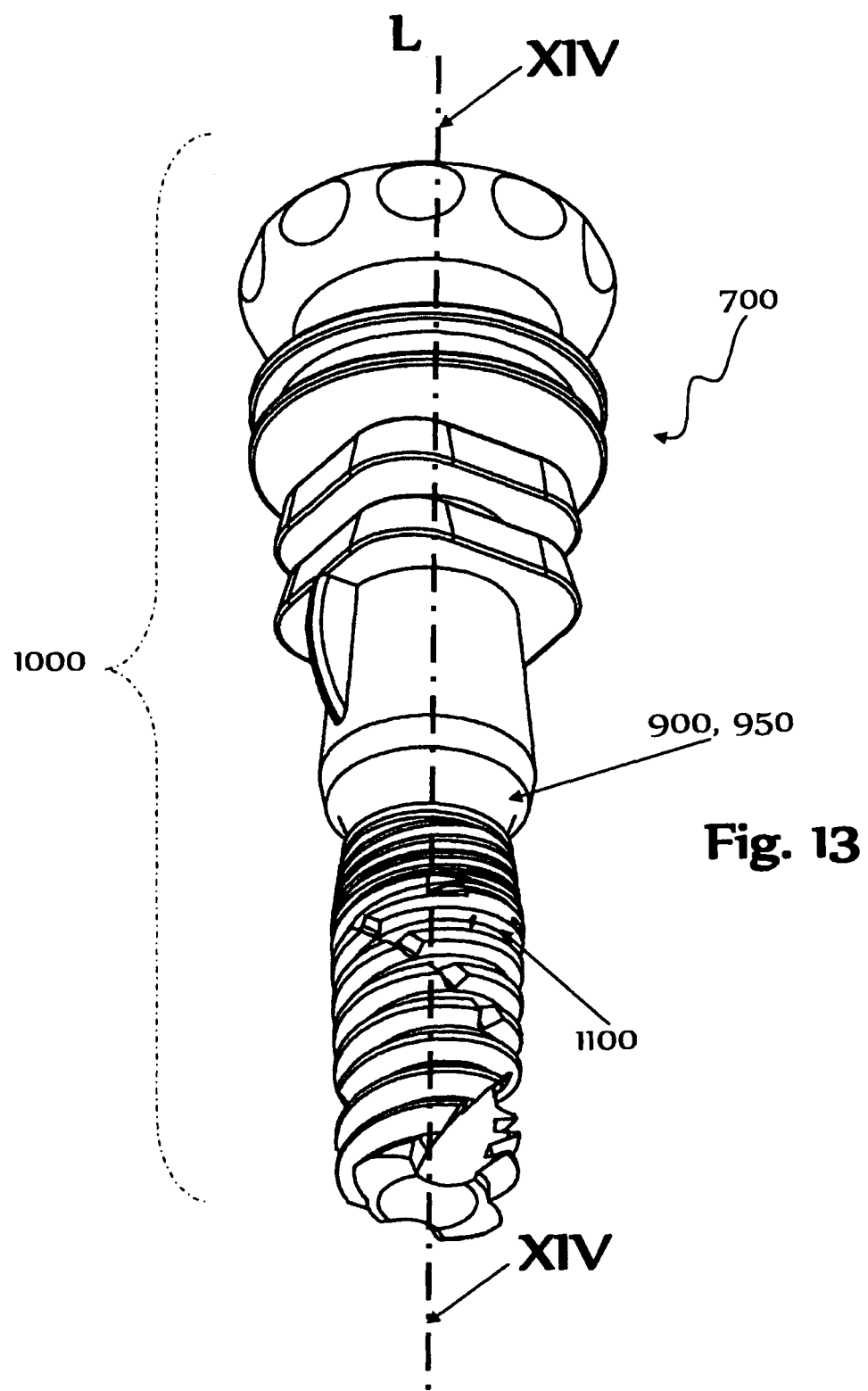
FIG. 13 schematically illustrates a bottom perspective view of the driver accommodating the implant assembly of FIG. 2.
Figure 14:
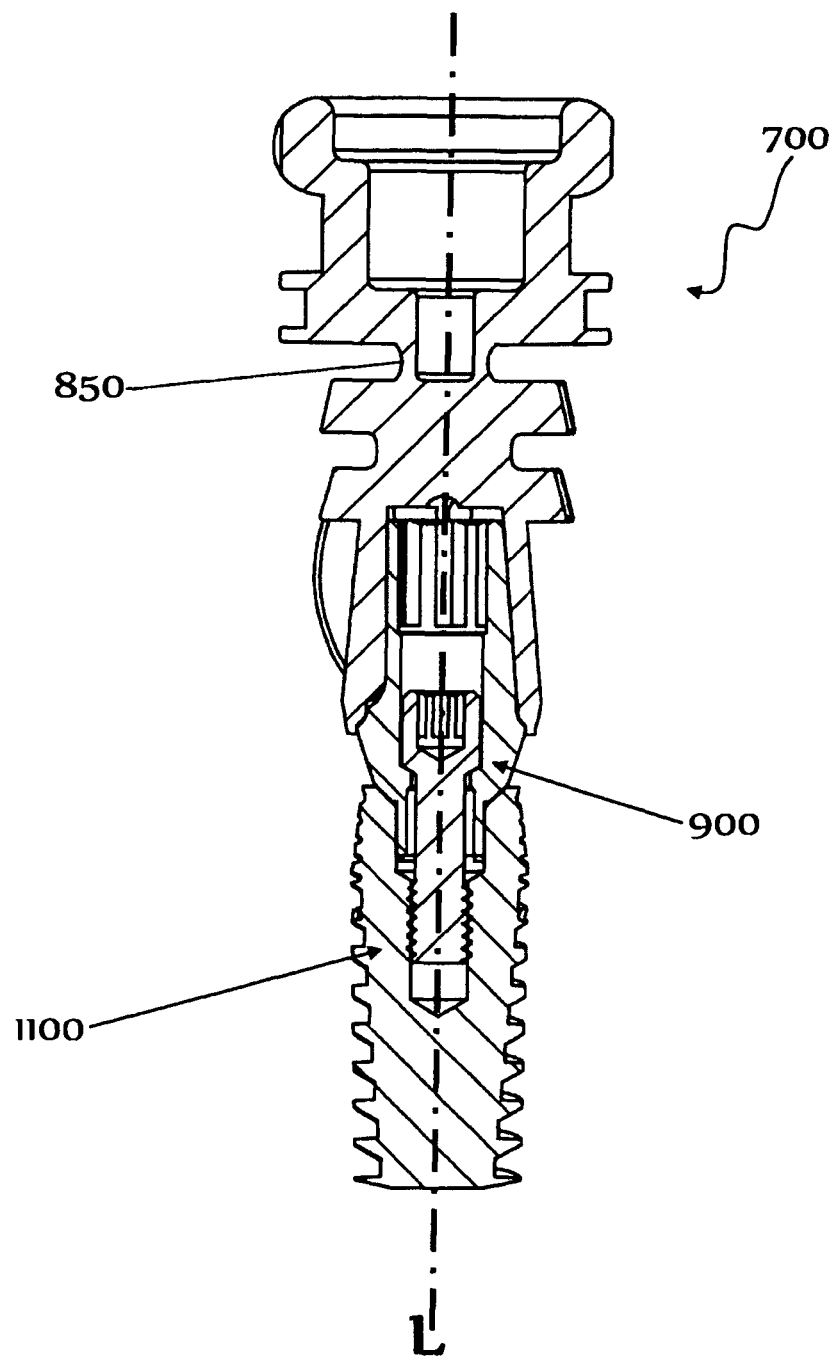
FIG. 14 schematically illustrates a longitudinal cross-sectional view taken in the plane XIV-XIV comprising the longitudinal axis L through the driver and implant assembly.

Attention is presently directed to FIG. 13 and FIG. 14. A driver assembly 1000 comprises the driver 700, with the cave 800 of the driver 700 accommodating the top member 930 of the abutment 900. An implant 1100 may be attached to the abutment 900 and may extend generally longitudinally away from the mid member 950 of the abutment 900.

Directing now attention additionally to FIG. 7a and FIG. 12a, the cave 800 of the driver 700 is designed to accommodate the top member 930 and the hump 934 of the abutment 900, with the welt 790 of the driver 700 resiliently grabbing a grab zone 952 disposed on the mid member 950. The grab zone 952 is disposed adjacent to, and extends away from, the hump 934 along the mid member 950. The grab zone 952 may be defined as a region where the end sector 798 grabs a portion of the mid member 950 adjacent the hump 934. The grab dimension $D_G$ is smaller than the hump dimension $D_H$, but is larger than the end dimension $D_E$ of the end sector 798.

Figure 11:
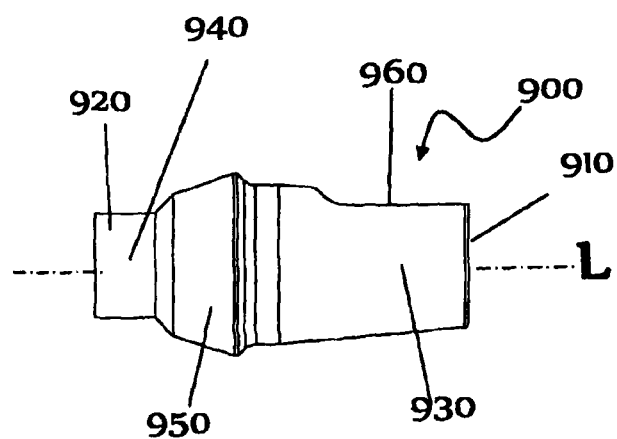
FIG. 11 schematically illustrates an elevation view of the abutment shown in FIG. 10.

Referring additionally to FIG. 7, FIG. 11 and/or FIG. 12, when the driver 700 accommodates the abutment 900, the flat face 960 of the abutment 900 rests upon the step-face 830 of the step 820 within the cave 800 of the driver 700. The flat face 960 and the step-face 830 may assist in limiting relative rotation between the driver 700 and the abutment 900. Resiliency of the driver's material, combined with the generally frusto-conical characteristic of the top member 930 of the abutment 900 may assist in expansion of the welt 790 when the abutment 900 is inserted into the cave 800 of the driver 700. During the final step of insertion, the hump 934 will be grabbed, between the first sector 796 and the end sector 798, as a result of the grabbing onto the grab zone 952 due to the resiliency of the material.

As the grab zone 952 is grabbed by the end sector 798, the top member 930 may be urged away from the end sector 798, thereby causing the flat face 960 of the top member 930 to abut the step-face 830 of the cave 800. Since the material of which the driver 700 may be made can be resilient, the rib 795 may offer increased resistance to the insertion of the top member 930 into the cave 800.

Referring now to FIGS. 2 to 14, the driver assembly 1000 is removably inserted to the hull 510 of the canister 500, and is accommodated within the second chamber 580 thereof. The driver assembly 1000 comprises the driver 700, the abutment 900, and an implant 1100 removably connected to the abutment 700. The driver assembly 1000 may also comprise the seal 1102 as shown, for clarity reasons, in FIG. 2, the seal 1102 optionally being an O-Ring type seal. The driver assembly 1000 may be inserted through the guide 582, with the head 730 and the neck 740 projecting away from the second opening 540. The bottom bank 754 rests against the step 586, with the seal 1102 being pressed against the opening wall 584, so as to seal the second chamber 580. The accessories 590 are assembled into the first chamber 570 and/or the re-movable cap 600, and are removably mounted within the first chamber 570 by means of the first opening 520. The assembled canister 500 may then be placed in the packaging 400, with the packaging 400 then closed by the lid 450.

Operation

Whenever practitioners need to transfer an implant 1100 to an implantation site, not shown, they may break open the packaging 400, for example, by removing the lid 450, and extracting the canister 500 from the fuselage 410. Once the canister 500 is extracted, the driver assembly 1000 may be extracted from the second chamber 580 of the hull 510. The extracted driver assembly 1000 may then be delivered to the implantation site, not shown, and driven, for example, by the practitioner's finger, or by an appropriate tool, both not shown in the drawings. When the implant 1100 held in the driver assembly 1000 is fully torqued-in, the driver 700 is intended to snap off at its stem 850, freeing the top section 710 from the bottom section 720 thereof.

All directional references, such as, but not limited to, upper, lower, up-ward, downward, left, right, leftward, rightward, top, mid or middle, bottom, above, midway, below, vertical, horizontal, clockwise, and counterclockwise, tangential, axial and/or radial, or any other directional and/or similar references, are only used for identification purposes to aid the reader's understanding of the embodiments of the present invention, and may not create any limitations, particularly as to the position, orientation, or use unless specifically set forth in the claims. Similarly, joinder references, such as, but not limited to, attached, coupled, connected, and the like, are to be construed broadly and may include intermediate members between a connection of elements and relative movement between elements. As such, joinder references may not necessarily infer that two elements are directly connected and in fixed relation to each other.

In some instances, components are described with reference to "ends" having a particular characteristic and/or being connected with another part. However, those skilled in the art will recognize that the present disclosure is not limited to components which terminate immediately beyond their points of connection with other parts. Thus, the term "end" should be interpreted broadly, in a manner that includes areas adjacent, rearward, forward of, or otherwise near the terminus of a particular element, link, component, part, member or the like.

Additionally, all numerical terms, such as, but not limited to, "first", "second", "third", or any other ordinary and/or numerical terms, should also be taken only as identifiers, to assist the reader's understanding of the various embodiments, variations and/or modifications of the present disclosure, and may not create any limitations, particularly as to the order, or preference, of any embodiment, variation and/or modification relative to, or over, another embodiment, variation and/or modification.

Similarly, adjectives such as, but not limited to, "articulated", "modified", or the like, should be construed broadly, and only as nominal, and may not create any limitations, particularly as to the description, operation, or use unless specifically set forth in the claims.

In methodologies directly or indirectly set forth herein, various steps and operations are described in one possible order of operation, but those skilled in the art will recognize that steps and operations may be rearranged, replaced, or eliminated without necessarily departing from the spirit and scope of the present disclosure as set forth in the claims. It is intended that all matter contained in the above description or shown in the accompanying drawings shall be interpreted as illustrative only and not limiting. Changes in detail or structure may be made without departing from the spirit of the present disclosure as defined in the appended claims.

While certain exemplary embodiments have been described and shown in the accompanying drawings, it is to be understood that such embodiments are merely illustrative of and not restrictive on the broad present disclosure, and that this present disclosure not be limited to the specific constructions and arrangements shown and described, since various other modifications and/or adaptations may occur to those of ordinary skill in the art. It is to be understood that individual features shown or described for one embodiment may be combined with individual features shown or described for another embodiment. It is to be understood some features are shown or described to illustrate the use of the present disclosure in the context of functional elements and such features may be omitted within the scope of the present disclosure and without departing from the spirit of the present disclosure as defined in the appended claims.

While certain exemplary aspects and/or embodiments have been broadly described and/or schematically illustrated in the accompanying drawings, it is to be understood that such aspects and/or embodiments are merely illustrative of, and not restrictive on, the broad present disclosure; further, those of skill in the art may recognize that the present disclosure may not be limited to the specific constructions and arrangements shown and described, since various other modifications, permutations, additions and sub-combinations may occur to those ordinarily skilled in the art, without detracting from the spirit and scope of the present disclosure. It is to be understood that individual features shown or described for one embodiment may be combined with individual features shown or described for another embodiment. Further, it is to be understood some features may have been shown or described to illustrate the use of the present disclosure in the context of functional anchoring elements and such features may be omitted within the spirit and scope of the present disclosure.

The invention claimed is:

1. A driving assembly for mounting a dental implant within an implantation site, comprising:
    an abutment assembly comprising an upper portion having a flat face formed thereon, and a lower portion adapted to be operatively connected to an implant so as to impress rotary torque upon the implant in order to implant the implant within an implant site; and
    a driver assembly defined around a longitudinal axis and having an upper driver portion, a lower driver portion having a cavity, defined by a first blind bore formed within said lower driver portion, for accommodating said upper portion of said abutment assembly, said cavity of said lower portion of said driver assembly having a flat step formed therein for mating with said flat face of said upper portion of said abutment assembly so as to effectively prevent relative rotation between said driver assembly and said abutment assembly whereby the implant can be implanted within the implant site as a result of rotational torque being transmitted from said driver assembly to said abutment assembly and from said abutment assembly to the implant, an annular groove, defined around an external portion of said driver assembly which is located at an axial position interposed between said upper driver portion and said lower driver portion, and a second blind bore defined within said upper driver portion and extending up to said axial position at which said external annular groove is defined so as to effectively define, with said external annular groove, an annular weakened stem having a decreased outer diameter and a decreased wall thickness relative to said upper and lower driver portions by means of which said upper driver portion of said driver assembly is separable from said lower driver portion of said driver assembly so as to be discarded while said lower driver portion of said driver assembly is retained upon said upper portion of said abutment assembly connected to the implant.

2. The driving assembly of claim 1, wherein:
said driver assembly is manufactured from a resilient and non-metallic material.

3. The driving assembly of claim 1, wherein:
said driver assembly is monolithic.

4. The driving assembly of claim 1, wherein:
said driver assembly comprises a welt having an inner welt wall extending away from a terminus at a bottom-most longitudinal extent of said driver so as to meet, and merge with, an inner wall of said cavity.

5. The driving assembly of claim 4, wherein:
said inner welt wall comprises a generally diverging frusto-conical first sector adjacent to and merging with said inner wall of said cavity, and a generally converging frusto-conical end sector adjacent to, and merging with, said terminus.

6. The driving assembly of claim 5, wherein:
said first sector diverges from a mouth dimension $D_C$ of said cavity to a first dimension $D_F$ adjacent to said terminus.

7. The driving assembly of claim 6, wherein:
said end sector converges from said first dimension $D_F$ to an end dimension $D_E$.

8. The driving assembly of claim 7, wherein:
said upper portion of said abutment assembly extends away from an upper tip portion so as to merge with a mid member of said abutment assembly at a circumferential expansion portion of said abutment assembly which is generally shaped as a frustum starting with a small dimension transverse to the longitudinal axis identical to a base dimension $D_B$ of said upper portion of said abutment assembly and expanding to a hump dimension $D_H$ at a hump portion of said circumferential expansion.

9. The driving assembly of claim 8, wherein:
said hump portion connects said expansion portion to said mid member.

10. The driving assembly of claim 9, wherein:
said mid member extends from said hump portion away from said upper portion of said abutment assembly towards said lower portion of said abutment assembly as said mid member converges from said hump dimension $D_H$ to a grab dimension $D_G$ of a grab zone of said abutment.

11. The driving assembly of claim 10, wherein:
said cavity of driver assembly is adapted to accommodate said upper portion and said hump of said abutment, with said welt of said driver assembly resiliently grabbing said grab zone of said abutment.

12. The driving assembly of claim 11, wherein:
said grab zone of said abutment assembly is disposed adjacent to, and extends away from, said hump along said mid member.

13. The driving assembly of claim 12, wherein:
said grab zone is defined as a region where said end sector of said driver assembly grabs a portion of said mid member adjacent to said hump.

14. The driving assembly of claim 13, wherein:
said grab dimension $D_G$ is smaller than said hump dimension $D_H$ and is larger than said end dimension $D_E$ of said end sector.

15. The driver assembly as set forth in claim 1, further comprising:
a second annular groove defined upon an external portion of said upper driver portion; and
an annular O-ring seal member disposed within said second annular groove for sealingly mating with a packaging cannis-ter.

16. A method of driving an implant into an implantation site, comprising the steps of:

providing an abutment assembly comprising an upper portion having a flat face formed thereon, and a lower portion adapted to be operatively connected to an implant so as to impress rotary torque upon the implant in order to implant the implant within an implant site;

providing a driver assembly defined around a longitudinal axis and having an upper driver portion, a lower driver portion having a cavity, defined by a first blind bore formed within said lower driver portion, for accommodating said upper portion of said abutment assembly, said cavity of said lower driver portion of said driver assembly having a flat step formed therein for mating with said flat face of said upper portion of said abutment assembly so as to effectively prevent relative rotation between said driver assembly and said abutment assembly whereby the implant can be implanted within the implant site as a result of rotational torque being transmitted from said driver assembly to said abutment assembly and from said abutment assembly to the implant;

forming an annular groove around an external portion of said driver assembly which is located at an axial position interposed between said upper driver portion and said lower driver portion;

forming a second blind bore within said upper driver portion and extending up to said axial position at which said external annular groove is defined so as to effectively define, with said external annular groove, an annular weakened stem having a decreased outer diameter and a decreased wall thickness relative to said upper and lower driver portions by means of which said upper driver portion of said driver assembly is separable from said lower driver portion of said driver assembly so as to be discarded while said lower driver portion of said driver assembly is retained upon said upper portion of said abutment assembly connected to the implant; and separating the upper driver portion from said lower driver portion so as to be discarded while said lower driver portion of said driver assembly is retained upon said upper portion of said abutment assembly connected to the implant.

* * * * *